US006613316B2

(12) United States Patent
Sun et al.

(10) Patent No.: US 6,613,316 B2
(45) Date of Patent: Sep. 2, 2003

(54) MONO AND DIALKYL QUATS IN HAIR CONDITIONING COMPOSITIONS

(75) Inventors: Wei-Mei Sun, Palatine, IL (US); Teresa Jolanta Dowell, Downers Grove, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/010,354

(22) Filed: Oct. 22, 2001

(65) Prior Publication Data

US 2002/0106343 A1 Aug. 8, 2002

Related U.S. Application Data

(60) Provisional application No. 60/244,096, filed on Oct. 27, 2000.

(51) Int. Cl.$^7$ ................................................ A61K 7/075
(52) U.S. Cl. ..................................... 424/70.28; 424/701
(58) Field of Search ............................... 424/701, 702.8

(56) References Cited

U.S. PATENT DOCUMENTS 4,818,523 A    4/1989   Clarke et al.
4,976,956 A    12/1990  Noe

FOREIGN PATENT DOCUMENTS

| DE | 195 38 094 C | 2/1997 |
| GB | 2316615 | 3/1998 |
| WO | 00/07562 | 2/2000 |
| WO | 00/48556 | 8/2000 |

OTHER PUBLICATIONS

International Search Report Application No. PCT/EP 01/12082 mailed Jul. 11, 2002.

Primary Examiner—Jyothsan Venkat
(74) Attorney, Agent, or Firm—Milton L. Honig

(57) ABSTRACT

The present invention relates to an aqueous opaque hair conditioner which comprises a monoalkyl quat from C14 to higher Carbon chain lengths (preferably C16 to C22) and a dialkyl quat which is a mixture of C16, C16 dialkyl quat and C18, C18 dialkyl quat. Also included is an amount of fatty alcohol to opacify the conditioner. Optionally, a silicone compound may be included. The monoalkyl quat may be in a ratio to the dialkyl quat of about 15:1 to about 2:1. The carbon chain lengths within the dialkyl quat are present in a weight ratio of about 1:3 to about 3:1 of C16,C16 to C18, C18. The fatty alcohol may be present in an amount from about 1% to about 10%.

20 Claims, No Drawings

MONO AND DIALKYL QUATS IN HAIR CONDITIONING COMPOSITIONS

RELATED APPLICATION

The present application claims the benefit of priority of prior copending provisional application, Ser. No. 60/244,096, filed Oct. 27, 2000.

BACKGROUND OF THE INVENTION

Most individuals buy and use a hair shampoo for its cleansing properties. In addition to having clean hair, a consumer also desires sufficiently-conditioned hair that holds a preset configuration. However, hair shampoos generally are formulated with highly effective anionic surfactants that primarily clean as opposed to conditioning the hair. Anionic surfactants not only remove the dirt and soil from the hair, but also remove lipids naturally present on the surface of the hair fibers. Therefore, the desirable cleansing properties of anionic surfactants also leave the hair in a cosmetically-unsatisfactory condition. Shampoos also do not help to detangle wet hair and do not impart residual conditioning benefits to dry hair, such as manageability or styleability of hair sets.

In general, shampoo compositions containing anionic surfactants, or nonionic surfactants or amphoteric surfactants, leave the hair with an undesirable harsh, dull and dry touch, or feel, usually called "creak", after the hair is shampooed and then rinsed with water. Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing property of dry hair remains poor, and the hair has undesirable electrostatic properties in a low humidity atmosphere that causes the hair to "fly away", thereby further reducing the brushing properties of the hair.

The unsatisfactory combing or brushing property of hair immediately after shampooing, or during trimming treatments after shampooing, also causes hair damage, such as split ends or hair breakage. In addition, the natural luster and resiliency of the hair is reduced. The overall unsatisfactory condition of shampooed hair often necessitates a subsequent post-shampoo treatment of the hair with a conditioning composition to improve these undesirable physical characteristics. Conditioning compositions typically are applied separately from the hair shampoo, and usually are rinses, cream-like emulsions or lotions containing a cationic compound.

Therefore, consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition, followed by a second rinse. The wet combing problem has been solved by treating shampooed hair with a conditioner composition that coats the hair shaft and causes the individual hair shafts in a tress to resist tangling and matting because of the smooth coating provided by conditioner molecules on the shaft.

However, the need for improved compositions that condition the hair, i.e., render the hair more manageable, has long been recognized in the art. As previously discussed, it is well-known that anionic surfactants are suitable for hair shampooing, and that cationic compounds, like cationic surfactants and cationic polymers, are useful as hair conditioners. Therefore, cationic compounds that are substantive to hair often are used to complete the hair cleansing and hair conditioning cycle.

The ability of cationic compounds to adsorb to or interact with the keratinous material of the hair makes these compounds desirable for improving wet hair detangling and dry hair manageability. However, cationic compounds that adsorb particularly strongly to the hair also can reduce the elasticity, body and set of the dried hair. Therefore, although conditioning compositions for application to freshly shampooed hair are well known, new and improved conditioning formulations based on cationic compounds are continually sought.

The following is a list of patents and patent applications in this field.

U.S. Pat. No. 4,818,523 discloses a stable easily removable hair rinse conditioner which provides good conditioning, styling ease, and manageability of hair, but does not build up and is cost effective, consisting essentially of effective amounts of a dodecyl trimethyl quaternary ammonium compound, a saturated or unsaturated $C_{14}$–$C_{22}$ alkanol, and a cyclic or linear silicone, in an aqueous vehicle.

U.S. Pat. No. 4,976,956 discloses a method of imparting improved conditioning properties to hair comprising treating the hair with a composition comprising a water-soluble quaternary ammonium compound, such as cetrimonium chloride; an oil-soluble, water-dispersible quaternary ammonium compound, such as distearyldimonium chloride; an acid-neutralized amidoamine compound, and a low molecular weight polydimethylsiloxane compound, such as cyclomethicone. The method and composition unexpectedly provide improved hair-conditioning properties such as wet feel, wet and dry combing, manageability, sheen, luster, body and overall hair condition.

U.S. Ser. No. 09/130,956 filed Aug. 7, 1998 discloses hair conditioning compositions comprising mono and dialkyl quats.

U.S. Ser. No. 09/252,564 filed Feb. 18, 1999 discloses hair conditioning compositions comprising silicones and mono and dialkyl quats.

There are a series of patents from Lion Corp that describe the use of a monoalkyl and a dialky quat mixture in a conditioner. These are Japanese Patents JP 56169617 A, JP 56169615 A, JP 87008088, JP 56169614 A, JP 87008087 B, JP 56169613 A, JP 87008086 B and U.S. Pat. No. 4,976,956.

The present invention is directed to an aqueous opaque conditioning composition that is esthetically acceptable to consumers, improves the wet combing and dry combing properties of hair, and also leaves the dry hair with satisfactory cosmetic and physical properties, including, in particular, dry combing and feel, less hair coating, manageability, body, condition of the ends and set.

SUMMARY OF THE INVENTION

The invention is an aqueous opaque conditioner that has a combination of two different types of conditioning agents and an emulsifier. The present invention is a low solids formulation that provides substantial conditioning benefit without compromising viscosity, to users who use conditioners.

The purpose of the invention is to provide a conditioner with improved performance, while using effective materials at ratios that optimize their benefit.

The present invention relates to an aqueous opaque conditioner which comprises a monoalkyl quat from C14 to higher Carbon chain lengths (preferably C16 to C22) and a dialkyl quat selected from a mixture of C16, C16 dialkyl quat and C18, C18 dialkyl quat. Also included is an amount of fatty alcohol necessary to opacify the conditioner.

Another aspect of the invention is to provide a method of treating the hair to yield well-conditioned hair having esthetically pleasing physical properties by contacting the hair with an aqueous opaque conditioner of the present invention.

The present invention relates to an aqueous opaque hair conditioning composition comprising:

(a) a monoalkyl quat having 14 or greater carbon atoms in an alkyl substituent; preferably the monoalkyl quat has 16 to 22 carbon atoms.

(b) and a dialkyl quat selected from a mixture of C16,C16 dialkyl quat and C18,C18 dialkyl quat;

(c) a silicone compound; and (d) a fatty alcohol in an amount sufficient to opacify said composition.

Another aspect of the invention is to provide a method of treating the hair to yield well-conditioned hair having esthetically pleasing physical properties by contacting the hair with an opaque conditioner of the present invention.

DETAILED DESCRIPTION OF THE INVENTION

Unless indicated otherwise, as used herein, "%" means weight %. The starting materials set forth herein are either known or can be prepared in accordance with known methods. As used herein, "C16, C16 dialkyl quat" or "C16 dialkyl quat" or "(Di—$C_{16}$) quat" refers to a quaternary ammonium compound wherein two of the alkyl substituents are the same and each of these alkyl substituents contains 16 carbon atoms. As used herein, "C18, C18 dialkyl quat" or "C18 dialkyl quat" or "(Di—$C_{18}$) quat" refers to a quaternary ammonium compound wherein two of the alkyl substituents are the same and each of these alkyl substituents contains 18 carbon atoms.

The current invention teaches a new and improved conditioning formulation based on cationic compounds in which enhanced wet and dry hair properties can be achieved. The technology relates to a low solids, cost-effective formulation that provides substantial conditioning benefit without compromising the sensory attributes to consumers.

The conditioning benefit obtained from a typical hair conditioner without silicone oil has been hypothesized to be due to deposition on hair of a lamellar gel structure formed from a mixture of alkyl quat (either monoalkyl or dialkyl quat) and fatty alcohol. Recently, it has been found that a mixture of monoalkyl quat and dialkyl quat of specific chain length can provide superior conditioning benefit compared to that provided by either monoalkyl or dialkyl quat alone. However, the wet and dry stage performance is still not comparable to the silicone oil-containing conditioners. This invention teaches a mixed monoalkyl quat (preferably C16 to C22) and dialkyl quat system in which the dialkyl quat contains mixtures of specific hydrocarbon chain lengths (preferably C16 to C18). Also included is a fatty alcohol in an amount sufficient to provide opacity and viscosity to the conditioner. It has been found that an enhanced wet and dry stage conditioning performance can be achieved by using mixed alkyl chain lengths within the dialkyl quat. This technology provides a route to deliver excellent wet and dry combing properties that is comparable to hair conditioners that contain silicone oils.

Without being bound by any particular theory, the compositions in the present invention show that in a mixed mono/di alkyl quat conditioner system, by incorporating a dialkyl quat that contains a mixture of different alkyl chain lengths into the lamellar gel phase, a superior wet-combing performance can be achieved. The wet combing performance is comparable to the silicone oil-containing conditioners.

The present invention relates to an opaque conditioner which comprises a monoalkyl quat from C14 to higher carbon chain lengths (preferably C16 to C22) and a dialkyl quat each alkyl of which is C16 or each of which is C18. Also included is an amount of fatty alcohol sufficient to opacify the conditioner. Also optionally included is a silicone compound such as an amodimethicone, dimethicone, or dimethiconol.

The following is a description of ingredients which can be included in compositions of the invention.

Monoalkyl Quats

Monoalkyl quats can be compounds of the formula $N^+R^1R^2R^3R^4X^-$ wherein $R^1$, $R^2$, and $R^3$ are C1–C3 alkyl groups and $R^4$ is a C14 or greater alkyl group (preferably C16 to C22); and $X^-$ is any acceptable counterion such as chloride, bromide, methosulfate, ethosulfate, nitrate, acetate, phosphate or tosylate.

Non-limiting examples of monoalkyl quats are:

cetyltrimethylammonium chloride (C16);

stearyltrimethylammonium chloride (C18);

behenetrimethylammonium chloride (C22);

cetyltrimethyl ammonium bromide (C16);

soytrimonium chloride (C18);

tallowtrimonium chloride (C16/C18);

behentrimethylammonium methosulfate (C22);

Peg-2 Olealmonium chloride (C18);

palmityltrimethylammonium chloride (C16);

hydrogenated tallowtrimethylammonium chloride (C16/C18);

hydrogenated tallowtrimethylammonium bromide (C16/C18);

hydrogenated tallowtrimethylammonium methosulfate (C16/C18);

cetrimonium tosylate (C16): and eicosyltrimethylammonium chloride (C20).

In compositions of the invention, said monoalkyl quat is selected from the group consisting of behentrimonium chloride and cetrimonium chloride, most preferably, cetrimonium chloride.

Monoalkyl quats are present in the composition from about 0.001 to 20% by weight, preferably from about 0.01 to 10% by weight, more preferably from 0.1 to 5% by weight, most preferably from about 0.5% to 2% by weight.

Dialkyl Quats

Dialkyl quats can be compounds of the formula $N^+R^5R^6R^7R^8X^-$ wherein $R^5$ and $R^6$ are C1–C3 alkyl groups and $R^7$ and $R^8$ are the same and each contains 16 carbon atoms; or $R^7$ and $R^8$ are the same and each contains 18 carbon atoms; and $X^-$ is any acceptable counterion such as chloride, bromide, methosulfate, ethosulfate, nitrate, acetate, phosphate; or tosylate.

Non-limiting examples of dialkyl quats are:

dicetyldimethylammonium chloride(C16);

distearyldimethylammonium chloride (C18);

dipalmityldimethylammonium chloride (C16);

dihyrogenatedtallowdimethylammonium chloride (C16/C18);

ditallowdimethylammonium chloride (C16/C18)

dihyrogenatedtallowdimethylammonium bromide (C16/C18)

dihyrogenatedtallowdimethylammonium methosulfate (C16/C18)

A mixture of dialkyl quats is used in compositions of the invention.

The dialkyl quat in compositions of the invention is a mixture of C16, C16 dialkyl quat and C18, C18 dialkyl quat. The quats can be selected from the group consisting of dicetyldimonium chloride and distearyldimonium chloride.

An important aspect of the invention is the use of a mixture of alkyl chain lengths within the dialkyl quat to achieve superior conditioning performance that can be comparable to silicone oil-containing conditioners.

The dialkyl quats within the dialkyl quat mixture, that is C16, C16 dialkyl quat and C18, C18 dialkyl quat, are present in a weight ratio of about 1:5 to about 5:1, preferably 1:4 to about 4:1, and most preferably 1:3 to about 3:1 and most preferably from about 1:2 to about 2:1. The C16 C16 dialkyl quat and C18 C18 dialkyl quat mixture may also have weight ratios of about 1:3 to about 2:1; 1:3 to about 1:1; 3:1 to about 2:1; 3:1 to about 1:1; and about 1:1.

Dialkyl quats are present in the composition at from about 0.001 to 20% by weight, preferably from about 0.01 to 10% by weight, more preferably from 0.1 to 5% by weight, most preferably from about 0.5% to 1% by weight.

The ratio of the monoalkyl quat to the mixture of dialkyl quats

The ratio of the monalkyl quat to dialkyl quat mixture in compositions of the invention is about 15:1 to about 2:1 or 1:1. The ratio of monalkyl quat to dialkyl quat in compositions of the invention may also be about 10:1 to about 2:1 or 1:1. The ratio of monalkyl quat to dialkyl quat in compositions of the invention may also be about 4–:1 to about 2:1 or 1:1.

Silicone Compounds

Silicone compounds may optionally be used in compositions of the invention. A silicone compound may be selected from the group consisting of amodimethicone, dimethicone and dimethiconol.

Non-limiting examples of silicone compounds are:

DC929;

Octamethylcyclotetrasiloxane (D4),

DC 2-1784,

DC 2-1780,

DC 2-949

DC 2-1784 and

Decamethylcyclopentasiloxane (D5).

Fatty Alcohols

Fatty alcohols may be present in compositions of the invention at about 1 to about 10%, more preferably at about 1 to about 5%, because at lower fatty alcohol levels there is better wet-stage combing performance of the compositions.

The following are non-limiting examples of fatty alcohols which may be used in the compositions of the invention:

cetyl alcohol (C16);

stearyl alcohol (C18);

cetearyl alcohol (C16/C18);

behenyl alcohol (C22);

arachidyl alcohol; and mixtures thereof.

The fatty alcohol is preferably cetearyl alcohol.

The fatty alcohol may be present in compositions of the invention in an amount sufficient to opacify the composition. For example, fatty alcohol may be present from about 1 to about 10% or, more preferably, from about 1% to about 5%.

Optional ingredients which may be included in the compositions of the invention are hydrocarbons such as paraffin, vaseline solid paraffin, squalene, oligomer olefins and the like; amidoamines such as stearamidopropyl dimethylamine, isostearamidoethyl morpholine, behenamidopropyl dimethylamine and the like; humectants such as glycerine, propylene glycol, glycerol, sorbitol and the like; esters, such as isopropyl palmitate, isopropyl myristate, and stearyl stearate and the like; emulsifiers such as glyceryl monostearate, sorbitan monopalmitate, polyoxyethylene stearate and the like; cellulose derivatives such as hydroxypropylcellulose; cationic cellulose, hydroxyethyl cellulose and the like; thickening agents such as natural polymers and the like; and other ingredients such as solvents, bacteriocides, colors, and fragrances.

Compositions of the invention may be prepared by methods which are known to those skilled in the art. Ingredients used in the preparation of compositions of the invention are either known or may be prepared by known methods.

Compositions of the invention are used to condition hair by first wetting the hair, applying the composition of the invention, lathering the hair, and then rinsing the hair. Alternatively, water and a conditioner of the invention may be applied to the hair simultaneously. Alternately, a conditioner of the invention may be applied first, and then water. Conditioning with compositions of the invention may be done right after shampooing when the hair is still wet. Alternatively, conditioning the hair with compositions of the invention may be done separately from shampooing.

Compositions of the invention provide unexpectedly superior conditioning benefits when compared with prior art formulations. Compositions of the invention unexpectedly provide a high, consumer acceptable viscosity using relatively low levels of monoalkyl quat, dialkyl quat, silicone compounds, and fatty alcohol.

Finally, compositions of the invention provide unexpectedly superior conditioning without the use of increased fatty alcohols.

To demonstrate the new and unexpected results achieved by the present invention, the following compositions were prepared. These compositions illustrate the invention and do not limit the invention. These compositions, along with experimental data, are shown in the tables below.

EXAMPLES

Compositions of the present invention have significantly more conditioning properties versus a formulation with ingredients that fall outside of the ratios set by the present invention. The table below illustrates this.

The objective of the experiment below was to evaluate the wet combing performance of centrimonium chloride (CTAC) based conditioner prototypes which contain 0.5% dialkyl quats with varying C16/C18 chain length ratios. The conditioners contain a 4:1 monoalkyl to dialkyl molar ratio with the dialkyl quat chain length being varied systematically as shown below.

| Composition A | 1:1 molar ratio C16:C18 dialkyl quat |
| --- | --- |
| Composition B | 24:76 molar ratio C16:C18 dialkyl quat |
| Composition C | 76:24 molar ratio C16:C18 dialkyl quat |
| Composition D | 63:37 molar ratio C16:C18 dialkyl quat |
| Composition E | 37:63 molar ratio C16:C18 dialkyl quat |
| Composition F | 100% C16 dialkyl quat |
| Composition G | 100% C18 dialkyl quat |

The above molar weight ratios of C16:C18 dialkyl quat of compositions A through F of the invention, fall within the weight % ratios of C16:C18 dialkyl that have been given above for compositions of the invention.

Experimental

Wet combing experiments were carried out on the Instron 5500 series. All testing was carried out by applying 0.3 mL of product to bleached and waved 2 g hair tresses. Results are expressed in terms of the maximum load (highest force encountered during combing) and combing energy (area under the combing curve). Commercial products, an Extra Moisturizing (XM) and a Bodifying conditioner (XB) that contain silicone oils in addition to cationic compounds, were also included in this study as internal controls. Wet combing results are given below.

Formulations and Intron Wet Combing Data

| | (Di-$C_{16}$/Di-$C_{18}$) quat mole ratio | | | | | | |
| --- | --- | --- | --- | --- | --- | --- | --- |
| Ingredients | 100/0 F | 74/26 C | 63/37 D | 1/1 A | 37/63 E | 26/74 B | 0/100 G |
| Cetrimonium chloride, 30% active | 2.8 | 2.8 | 2.8 | 2.8 | 2.8 | 2.8 | 2.8 |
| Dipalmityldimonium chloride | 0.38 | 0.28 | 0.24 | 0.19 | 0.14 | 0.10 | — |
| Distearyldimonium chloride | — | 0.10 | 0.14 | 0.19 | 0.24 | 0.28 | 0.38 |
| Cetearyl alcohol[1] | 3.0 | 3.0 | 3.0 | 3.0 | 3.0 | 3.0 | 3.0 |
| Potassium chloride | 0.3 | 0.3 | 0.3 | 0.3 | 0.3 | 0.3 | 0.3 |
| Disodium EDTA | 0.1 | 0.1 | 0.1 | 0.1 | 0.1 | 0.1 | 0.1 |
| Other[2] | Q.S. | Q.S. | Q.S. | Q.S. | Q.S. | Q.S. | Q.S. |
| Instron Wet-combing Combing Force (gram force)* | 11.6 | 9.9 | 9.8 | 8.8 | 9.9 | 10.4 | 14.5 |

Compositions A, B, C, D, and E of the invention can be made by methods which are known in the art, and were made as follows:

1. Add half of the de-ionized water to a beaker. Start agitation and begin heating to 170–175° F.;
2. At 145° F. add Cetrimonium chloride and at 150° F. add dipalmityldimonium/distearyldimonium chloride mixture until all of mixture is dissolved;
3. At 160° F. or above add cetearyl alcohol;
4. When batch temperature reaches 170–175° F., emulsify the batch for 30 minutes;
5. Start cooling the batch to 150° F. and add the desired amounts of cooling water;
6. A pre-mix of Disodium EDTA and KCl in water, is heated to 135–140° F. and mixed until completely dissolved;
7. When batch temperature reaches to 120° F., add salt pre-mix slowly and mix well;
8. At 110° F. add the remaining ingredients.

*:Combing force for the controls are: XM 9–10 gram force; XB 13.5–14.5 gram of force.

Cetearyl alcohol[1]: Alfol 16/18, a mixture of 60% $C_{16}OH$ and 40% of $C_{18}OH$; Henkel, Cincinnati, Ohio Other[2]: de-ionized water, fragrance, preservatives and other minor ingredients.

Compositions A, B, C, D, and E had significantly less wet combing force (and hence better conditioning properties) than compositions F and G.

What is claimed is:

1. An aqueous opaque hair conditioning composition comprising:
   (a) a monoalkyl quat having 14 or greater carbon atoms in an alkyl substituent;
   (b) a dialkyl quat which is a mixture of a C16, C16 dialkyl quat and C18, C18 dialkyl quat present in a weight ratio of about 1:3 to about 3:1; and
   (c) a fatty alcohol in an amount sufficient to opacify said composition.

2. A composition according to claim 1 wherein C16,C16 dialkyl quat and C18, C18 dialkyl quat are present in a weight ratio of about 1:2 to about 2:1.

3. A composition according to claim 1 wherein C16,C16 dialkyl quat and C18, C18 dialkyl quat are present in a weight ratio of about 1:3 to about 2:1.

4. A composition according to claim 1 wherein —C16, C16 dialkyl quat and C18, C18 dialkyl quat are present in a weight ratio of about 1:3 to about 1:1.

5. A composition according to claim 1 wherein C16,C16 dialkyl quat and C18, C18 dialkyl quat are present in a weight ratio of about 3:1 to about 2:1.

6. A composition according to claim 1 wherein C16,C16 dialkyl quat and C18, C18 dialkyl quat are present in a weight ratio of about 3:1 to about 1:1.

7. A composition according to claim 1 wherein —C16, C16 dialkyl quat and C18, C18 dialkyl quat are present in a weight ratio of about 1:1.

8. A composition according to claim 1 wherein the ratio of (a) to (b) is about 15:1 to about 2:1.

9. A composition according to claim 1 wherein the ratio of (a) to (b) is about 10:1 to about 2:1.

10. A composition according to claim 1 wherein the ratio of (a) to (b) is about 4:1 to about 2:1.

11. A composition in accordance with claim 1 wherein said fatty alcohol is present at about 1 to about 10%.

12. A composition in accordance with claim 1 wherein said fatty alcohol is present at about 1 to about 5%.

13. A composition in accordance with claim 1 wherein said monoalkyl quat is selected from the group consisting of behentrimonium chloride and cetrimonium chloride.

14. A composition in accordance with claim 1 wherein said dialkyl quat is a mixture of dicetyldimonium chloride and distearyldimonium chloride.

15. A composition in accordance with claim 1 wherein said monoalkyl quat is cetrimonium chloride.

16. A composition in accordance with claim 1 wherein said C18, C18 dialkyl quat is distearyldimonium chloride.

17. A composition in accordance with claim 1 wherein said fatty alcohol is cetyl alcohol.

18. A method for conditioning hair which comprises contacting hair with a composition of claim 1.

19. A composition in accordance with claim 1 further comprising a silicone compound.

20. An aqueous opaque hair conditioning composition comprising:

(a) a monoalkyl quat having 14 or greater carbon atoms in an alkyl substituent;
(b) a dialkyl quat which is a mixture of a C16, C16 dialkyl quat and C18, C18 dialkyl quat present in a weight ratio of about 1:3 to about 3:1;
(c) a silicone compound; and
(d) a fatty alcohol in an amount sufficient to opacify said composition.

* * * * *